United States Patent [19]

Judy et al.

[11] 4,440,638
[45] Apr. 3, 1984

[54] SURFACE FIELD-EFFECT DEVICE FOR MANIPULATION OF CHARGED SPECIES

[75] Inventors: Millard M. Judy; John L. Sutko, both of Dallas, Tex.

[73] Assignee: U.T. Board of Regents, Austin, Tex.

[21] Appl. No.: 348,988

[22] Filed: Feb. 16, 1982

[51] Int. Cl.³ .............................................. B01D 15/08
[52] U.S. Cl. .................................. 210/198.2; 55/155; 204/290 R; 204/302; 210/198.1; 210/748; 210/205
[58] Field of Search ..................... 210/746, 748, 198.1, 210/198.2, 223, 243; 204/20, 22, 290 R, 290 F, 204/302; 55/155

[56] References Cited

U.S. PATENT DOCUMENTS

| | | | |
|---|---|---|---|
| 2,364,118 | 12/1944 | Wolfe | 204/302 X |
| 4,020,830 | 5/1977 | Johnson et al. | 128/2 E |
| 4,180,771 | 12/1977 | Guckel | 324/71 |
| 4,214,981 | 7/1980 | Giddings | 210/748 X |
| 4,255,247 | 3/1981 | Oda et al. | 204/290 R |
| 4,358,379 | 11/1982 | Inoue | 210/742 X |

OTHER PUBLICATIONS

Gingell, D. and J. A. Fornes., Interaction of Red Blood Cells With a Polarized Electrode. Evidence of Long-Range Intermolecular Forces. Biophysical 1976, J. 16:1131.
Gingel, D. & I. Todd; Adhesion of Red Blood Cells to Charged Interfaces Between Imiscible Liquids. A New Method. J. Cell. Sci. 18:227, 1975.
Fay, F. S., P. H. Cooke & P. G. Canaday. Contractile Properties of Isolated Smooth Muscle Cells. in *Physiology of Smooth Muscle*, E. Bulbring and M. F. Shuba, Eds. Raven Press, New York, 1976.
Bioradiations, No. 31, Aug. 1979. Published by the Chemical Division of Bio-Rad Laboratories. p. 1, Bio-Carriers.
Hannig, K. and H. G. Heidrich. The Use of Continuous Preparative Free-Flow Electrophoresis For Dissociating Cell Fractions and Isolation of Membraneous Components. Meth. Enzymol. 31:746, 1974.
Giddings, J. C., S. R. Fisher and M. N. Myers. Field-Flow Fractionation. One-Phase Chromatography for Macromolecules and Particles. American Laboratory, May, 1978, p. 15.
Jacobson, B. S., Isolation of Plasma Membranes From Eukaryotic Cells in Polylysinecoated Polyacrylamide Beads. Biochem. Biophys. Acta. 471:331, 1977.
Kinoshita, T., R. L. Nachman and R. Minick. Isolation of Human Platelet Plasma Membranes With Polylysine Beads. J. Cell. Biol. 82:688, 1979.
Bioradiations, No. 31, p. 3, Affi-Gel 731-Isolates Cell Membranes. Published By the Chemical Division of Bio-Rad Laboratories.
Kaiser, N., Laser Absorption Spectroscopy With An ATR Prism. IEEE Transact. Biomed. Engn. 26:597, 1979.
Todd, I. and D. Gingell. Red Blood Cell Adhesion. I. Determination of the Ionic Conditions For Adhesion to an Oil-Water Interface. J. Cell. Sci. 41:125, 1980.
Gingell, D. and I. Todd., Red Blood Cell Adhesion. II. Interferometric Examination of the Interaction With Hydrocarbon, Oil and Glass. J. Cell. Sci. 41:135, 1980.
Parsegian, V. A. and D. Gingell. Red Blood Cell Adhesion. III. Analysis of Forces. J. Cell. Sci. 41:151, 1980.

*Primary Examiner*—John Adee
*Attorney, Agent, or Firm*—Arnold, White & Durkee

[57] ABSTRACT

A device capable of manipulating, sorting, separating and measuring the properties of charged species particles by physical interaction via electrostatic forces. The device operates on charged species particles ranging from small molecular species to intact mammalian cells. The device has a semiconductor substrate serving as an electrode. A dielectric layer overlays the substrate. A chamber holds a fluid which contains the charged species particles. The fluid in the chamber is placed in physical contact with the dielectric layer. A control electrode of metal is disposed opposite the dielectric layer and is also in physical contact with the fluid. A voltage source establishes an electric field between the electrodes which extends into the liquid. Charged species particles are either attracted to or repelled from the dielectric layer surface. The device structure readily provides for precise and continuous control of the electric field at the dielectric layer-fluid boundary interface. The electric field can be of either polarity and can be maintained with low levels of current flow.

7 Claims, 7 Drawing Figures

SURFACE FIELD-EFFECT DEVICE FOR MANIPULATION OF CHARGED SPECIES

BACKGROUND OF THE INVENTION

The present invention relates to devices for interacting with biological species; and more particularly, it relates to devices for physically interacting with charged species via electrostatic forces.

It has been demonstrated in the art that attractive and repulsive electrostatic forces underlie the initial interactions between biological cells and a well-defined surface. Gingell and Fornes in "Interaction of Red Blood Cells with a Polarized Electrode", *Biophysical Journal*, Vol. 16, page 1131 (1976), discuss the adhesion of glutaraldehyde—fixed human red blood cells to a smooth polarizable lead electrode in dilute sodium fluoride solution. The use of electrostatic interaction between chemical species to hold cells has been commercially implemented by Bio-Rad Laboratories, 2200 Wright Avenue, Richmond, Calif. 94804 in its BIO-CARRIERS ® microcarrier cell culture to hold cells. No manipulative control over cells has been provided, however.

Methodology for separating charged macromolecules and particulate species, including biological entities, to a large extent has its basis in electrostatic interactions, for example, electrical field-flow fractionation (FFF) which utilizes electrical potential differences. FFF is an elution method relying on the fractionation of solutes while moving through a channel. As the carrier stream moves through the channel, an external electrostatic force field is applied at right angles to the flow. The field interacts with the solute and forces it against the channel wall forming a layer. The mean thickness of the layer differs for each distinct chemical or particulate species, thereby providing a basis for selective retention, and produces an elution spectrum.

Another method for separation of charged species is electrophoresis. In this method, charged molecules are moved through a suitable medium by an electric field which permeates the medium. The molecules are separated on the basis of different electrophoretic mobilities.

It is also known to separate molecules according to charge using ion exchange chromatography. In this method, a column packing is used which consists of an insoluble support, charged functional groups covalently bound to the support, and mobile counterions which associate with the functional groups because of an opposite charge. When a mixture is passed through the column, molecules of neutral or like charge to the functional groups are eluted while oppositely charged molecules compete with the counterions for binding sites on the functional groups. Molecules more highly charged than the counterions become bound to the matrix and are retained on the column. An eluant having an appropriate ionic strength and pH is used to recover the bound sample. An example of how a variable system can greatly augment the sensitivity of such separations is that of isoelectric focusing. In this technique, the electrophoretic differences between compounds are coupled to their inherent differences in the pH at which their electrical charges are neutralized.

The existing techniques and devices based on electrostatic interaction with charged species do not offer the capabilities of continuous and dynamic control of the electrostatic field. That is, electrostatic interaction in these processes is neither continuously variable nor reversible. Moreover, the known techniques do not lend themselves to practical implementation in a small volume instrument. Further, due to the physical contact of both electrodes with a conducting medium, significant current flow occurs during the generation of an electrostatic field. Although electrostatic interaction with biological cells has been applied as a mechanism for the manipulation of cells, such as cell sorting, this approach due to the above-noted limitations has yet to be fully exploited, particularly on the level of an individual cell.

SUMMARY OF THE INVENTION

The present invention provides a device which selectively attracts charged species particles through electrostatic interaction to a liquid-solid dielectric interface in a controlled fashion. As used herein, the term "charged species" includes charged ions, molecular species, organelles, and biological cells.

The device of the present invention is characterized in that an electrically-conductive fluid containing charged species interfaces with a dielectric layer at one boundary surface and a control electrode at an opposing boundary surface. On the opposite side of the dielectric layer is a second electrode. A variable electric potential is established between the electrodes to produce a variable and reversible electric field extending into the fluid.

In operation of the device, charged species present in the fluid will either be attracted or repelled from the surface of the dielectric layer, depending upon the algebraic sign (+ or −) of the potential applied to the control electrode and the charge (+ or −) of a species particle. If the attractive force exerted on a charged species particle by the electric field exceeds the sum of the forces acting to repel the particle away from the dielectric layer boundary surface, the particle will be moved to that interface and held there so long as the balance of forces remains unchanged. Upon a decrease in the magnitude of the electric field, such that the attractive force on the particle becomes less than the sum of the repelling forces, the particle will no longer be held at the interface. Additionally, if the polarity of the electric potential applied to the control electrode is reversed, the electric field will reverse and particles previously attracted to the dielectric boundary will be repelled.

The force exerted on a charged species particle will be a function of the magnitude and algebraic sign of the charge of the particle and of the electric field. Therefore, by adjustment of the electric field strength, charged species particles may be selectively attracted or repelled on the basis of the inherent charge of the particle, as well as charge sign.

The device preferably comprises a second electrode which forms a substrate for the dielectric layer. The substrate electrode preferably is a semiconductor material, such as silicon. The dielectric layer may be silicon nitride, silicon dioxide or silicon carbide, or some combination thereof. The control electrode of the device preferably is a metal material, such as platinized platinum.

The substrate electrode can be precisely formed in a variety of shapes utilizing orientation-dependent etching techniques. For example, the substrate may be provided with grooves or channels therein having the dielectric layer uniformly formed over the channel surfaces. With such a substrate, the surface area available for interaction with charged species is significantly increased.

The device of the present invention has particular utility in cellular research. For example, cells can be sorted on the basis of their surface charge. Also, individual cells can be manipulated without adverse effect on cellular characteristics.

BRIEF DESCRIPTION OF THE DRAWING

A written description setting forth the best mode presently known for carrying out the present invention, and of the manner of implementing and using it, is provided by the following detailed description of illustrative embodiments shown in the attached drawing figures wherein.

DETAILED DESCRIPTION

Figure 1:
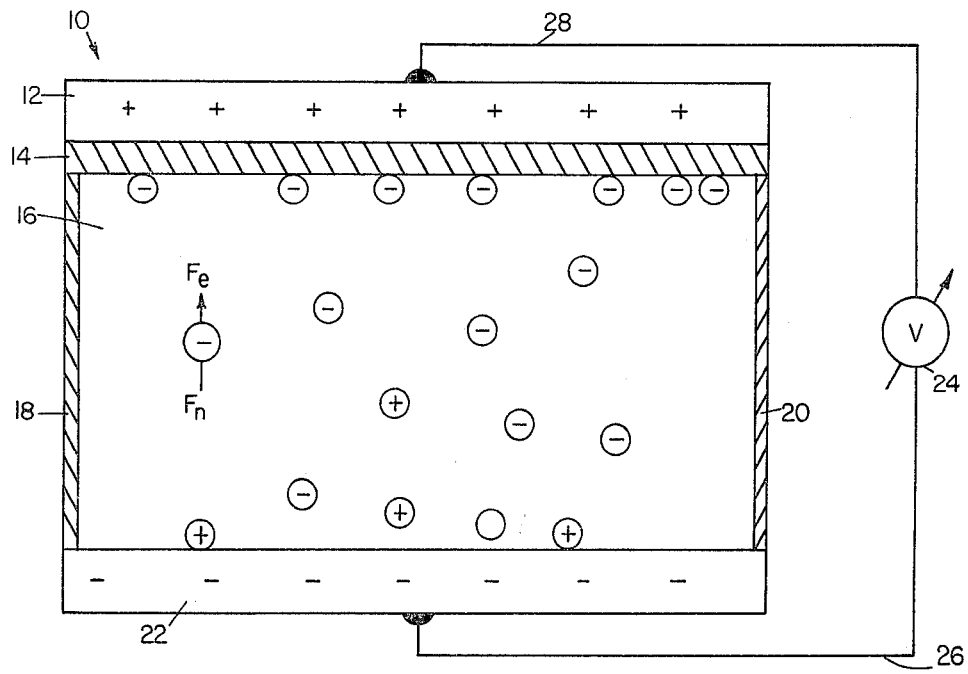
FIG. 1 is a cross-sectional view of a device in accordance with the present invention for controlled electrostatic force interaction with charged species particles.

Referring to FIG. 1, there is shown the basic structure of a device in accordance with the present invention for controlled electrostatic force interaction with charged species. Device 10 comprises an electrically-conducting substrate 12. Overlaying substrate 12 is a dielectric layer 14. A chamber 16 for holding a body of electrically-conducting fluid containing charged species is defined by walls 18, 20. As will be appreciated, the drawing of FIG. 1 presents a cross-sectional view of device 10. Accordingly, it is to be understood that walls 18 and 20 are but a portion of a continuous boundary wall which defines chamber 16. The fluid in chamber 16 is in direct physical contact with the surface of dielectric layer 14 to define a boundary interface. A control electrode 22 is spaced-apart from and opposite dielectric layer 14. The surface of electrode 22 is in physical contact with the fluid in chamber 16, and defines a second boundary interface.

A source 24 of electrical potential is connected across device 10 by having a first conductor 26 connected to electrode 22 and a second conductor 28 connected to substrate 12 which acts as an electrode. Preferably, source 24 is a variable DC voltage source. Source 24 provides a means for generating an electrical field between electrodes 12 and 22, which electric field extends into the fluid in chamber 16. Furthermore, with a variable voltage source, the magnitude and polarity of the electric field may be controlled.

Charged species particles in the presence of an electrical field will have exerted thereon a force. If the electric field is established by a direct current electric field generator, such as source 24, the force exerted on the charged species particle will be an electrostatic force, $F_e$. Charged species particles will also have non-electrical forces exerted thereon, for example, a gravitational force, $F_n$. Accordingly, for a charged species particle placed in an electric field, there will be a net force exerted on the particle which is the algebraic sum of the force components. For example, as shown for the case of negatively-charged species particles in FIG. 1, the electrical force is directed so as to attract charged species and the non-electrical force is oppositely directed, then only particles having a surface charge such that $F_e$ is greater than $F_n$ will be drawn to and held at the surface of the dielectric layer. Other charged particles of lesser charge will drift away under the influence of the stronger gravity force component. In this example, positively-charged species would be acted upon by the sum of the forces $F_n + F_e$.

The substrate electrode 12 is a semiconductor material. Preferably, silicon is used. The dielectric layer 14 may suitably be compounds such as silicon nitride, silicon dioxide or silicon carbide. Control electrode 22 may suitably be a metal material, such as platinized platinum.

Device 10 may be utilized to separate charged species particles contained in the fluid in chamber 16. The separation may be made on the basis of the relative magnitude of particle charge. Also, if charged species particles having net surface charges of different algebraic sign are present, device 10 provides for separation according to the algebraic sign or polarity of surface charge.

The electrical force, $F_e$, exerted on a charged particle is proportional to surface charge density, electric field strength, and particle size. For particles of the same physical size, separation may be made on the basis of net surface charge density by adjusting the electric field strength. Adjustments in the electric field strength can, of course, be made by changing the voltage applied to establish the electric field.

In one method of separating and collecting charged species particles, using device 10, the voltage of source 24 is adjusted to establish an electric field strength sufficient to attract to the dielectric layer surface charged species particles having a charge density of a minimum charge density above a certain threshold. In another method, device 10 may be used to separate and collect particles having a maximum charge density below a certain threshold. Separation proceeds adjusting the applied voltage so as to attract all charged species particles to the dielectric layer surface, and then decreasing the electric field strength such that particles of less than the threshold level of charge density drift away from the dielectric layer surface and are collected.

The operability of a device in accordance with the present invention has been established in experimentation in connection with charged species particles comprising mammalian red blood cells suspended in a fluid comprising an isotonic saline solution. The red blood cell-containing fluid was placed in a chamber formed by acrylic plastic sheet walls of a device constructed in accordance with device 10, as shown in FIG. 1. A battery was used to generate either a positive or a negative electrical field. It was found that the negative charged red blood cells could selectively be attracted to or repelled from the dielectric layer surface.

In practical implementation of device 10 for applications involving manipulation of charged species particles comprising biological cells, suitable device dimensions would have a chamber volume of 0.039 cm$^3$, a substrate thickness of 0.3 mm, a dielectric layer thickness of 0.15 microns, a dielectric layer surface area of 0.0079 in², and a control electrode of 0.005 inches thickness and 0.0079 in² surface area. The voltage source potential would suitably be variable over a range of +3.6 volts to −3.6 volts.

The substrate electrode may also be formed in various configurations and with various surface topographies through selective etching. Formation of the substrate, particularly the surface contour, may be in accordance with the teachings found in U.S. Pat. No. 4,065,742, titled COMPOSITE SEMICONDUCTOR STRUCTURES, and in "VERTICAL ETCHING OF SILICON AT VERY HIGH ASPECT RATIOS", Ann. Rev. Mater. Sci., 9:373–403 (1979).

The basic device structure shown and described herein may suitably be implemented for use in various research and clinical applications. The device may, for example, be used in cell sorting based on surface charge. The device may be used to exercise manipulative control over cells, such as cell immobilization, to facilitate measurements thereon or processing. The device may be used as a sensitive probe in cell function testing in situations wherein surface charge on a cell is a factor in cellular functioning. Also, the device may be used to form electrostatic interaction with intact tissue, such as the walls of blood vessels or of the heart, so as to stabilize the placement of catheters during clinical assessment procedures.

It is to be understood that the above-described device is only illustrative of the principles of the present invention, and that numerous embodiments may be devised by those skilled in the art for particular applications.

Figure 2:
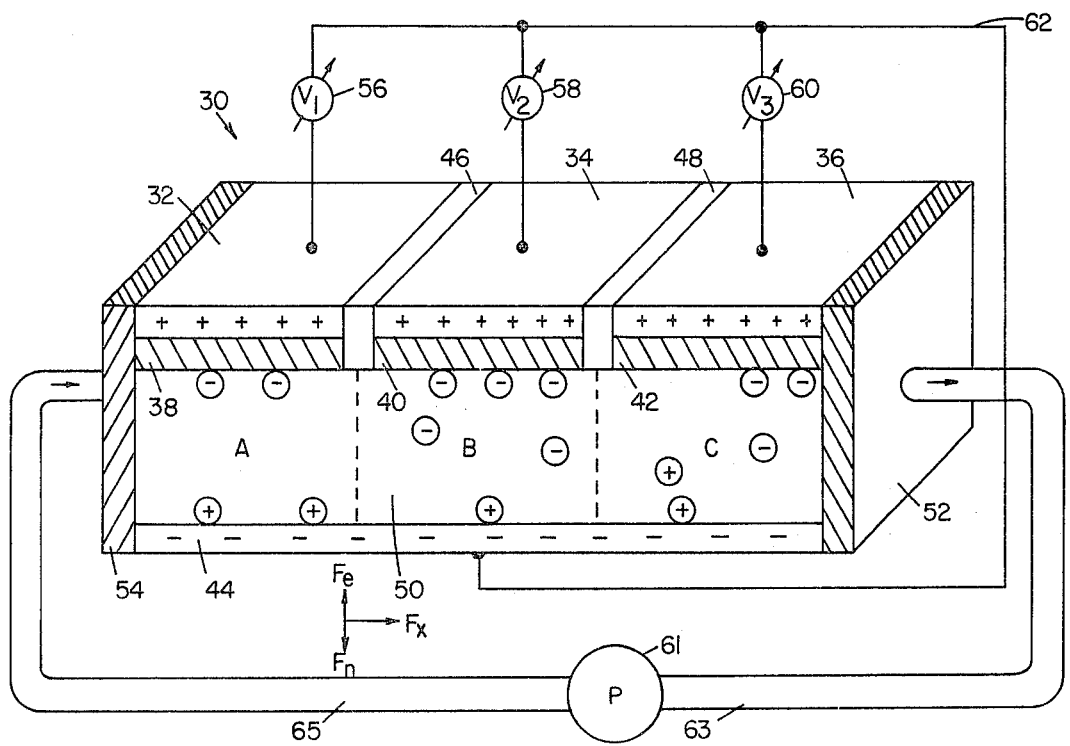
FIG. 2 is a perspective view of a device in accordance with the present invention for separation of charged species particles on the basis of surface charge and size.

Referring now to FIG. 2, there is shown an embodiment of the basic device concept for making a separation of charged species particles on the basis of surface charge and size.

The force, $F_n$, on a particle due to gravity is proportional to the volume or size of the particle which is a function of $R^3$, where R is the radius of the particle. In the presence of an electric field, the electrical force, $F_e$, acting on a charged particle is proportional to $R^2$ for a constant surface charge density and magnitude. Using these properties, it is possible to effect a separation of charged species particles on the basis of both size and net surface charge density using a device such as device 30 in FIG. 2.

Device 30 comprises three isolated electrically-conducting substrates 32, 34 and 36. Overlaying each substrate is a respective dielectric layer 38, 40 and 42. A single electrode 44 is spaced-apart from and opposite the dielectric layers. Isolation between adjacent substrate/dielectric layer structures is provided by vertical walls 46, 48 of a suitable isolating material. By reason of the isolation walls 46 and 48 between the adjacent substrate/dielectric layer structures, separate regions A, B and C are established within the chamber 50 of device 30, although the internal chamber volume is continuous between end walls 52 and 54.

Separate sources 56, 58 and 60 are connected to device 30. First source 56 having a potential $V_1$ connects to substrate 32. A second source 58 of potential $V_2$ connects to substrate 34, and a third source 60 of potential $V_3$ connects to substrate 36. A common connection 62 exists between sources 56, 58 and 60 and electrode 44. Electrical potential sources 56, 58 and 60 are individually adjustable to provide for the establishment of different electric fields in each of the regions A, B and C. Each of the regions of device 30 operates substantially in accordance with the single region device shown and described in connection with FIG. 1.

In order to effect a separation of charged species particles on the basis of both size and net surface charge density, the electric field strengths in each region will be established to set $F_e$ to a level so as to attract and hold all particles of the same sign at the dielectric layer. Then, a transverse laminar fluid flow is established to impose a translational force, $F_x$, on the particles to effect a separation according to size. Under the influence of $F_x$, smaller particles will travel a greater distance than larger particles, thereby placing particles of different sizes at different regions in device 30. Finally, the electric field established in a region is individually diminished allowing the particles in the region to settle away from the dielectric layer under the influence of gravity and be collected according to net surface charge.

Laminar flow can be established within device 30, for example, by a pump 61 and conduits 63, 65 interconnecting the pump with the chamber 50 through walls 52, 54.

Device 30 can be fabricated using conventional silicon processing practices. In accordance with the teaching of U.S. Pat. No. 4,065,742, already incorporated herein by reference, a silicon slice may be etched to provide grooves for receiving an insulating material such as silicon oxide. The structure then undergoes lapping and polishing to establish a planar surface over both oxide and silicon. The dielectric layer is established using a conventional method such as a thermal oxide and nitride MOS process, a chemical vapor deposition of silicon nitride or silicon carbide, or plasma deposition of silicon nitride. Finally, electrical contacts and metallization on each discrete region are formed using standard techniques.

Figure 3:
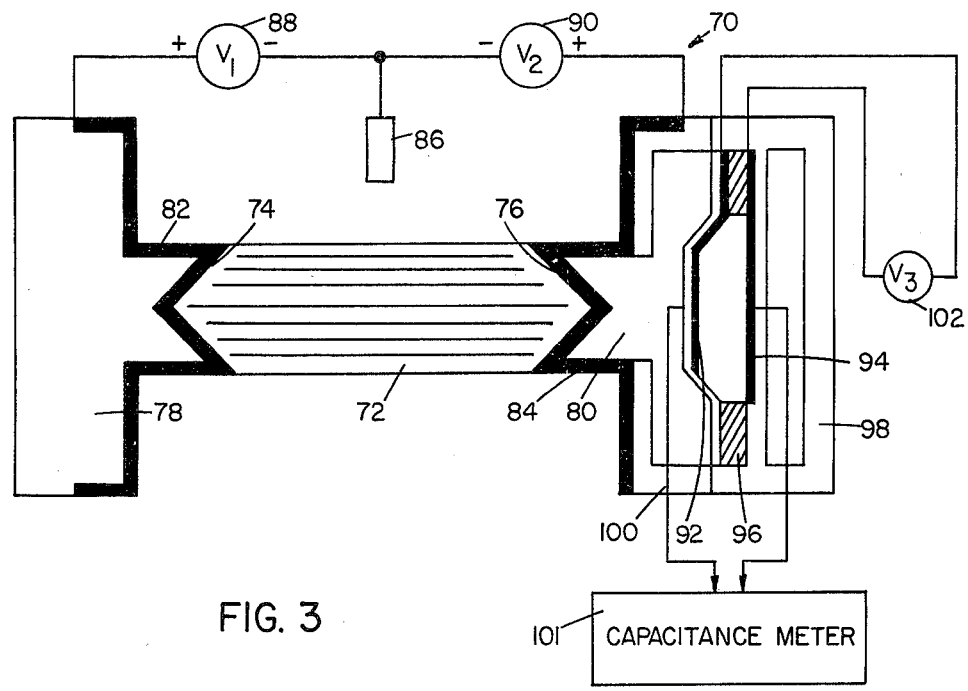
FIG. 3 is a schematic diagram of an embodiment of the present invention for holding and manipulating a single cell.

In FIG. 3, there is shown an embodiment of the present invention for holding and manipulating a single cell. Device 70 is shown holding a muscle cell 72 which has the capacity to generate force by shortening its length. Accordingly, muscle cell 72 has a functional parameter which can be measured. Device 70 provides for the measuring of the muscle force generating parameter.

Muscle cell 72 is held at each end in a pyramidal-shaped depression 74, 76 etched into a respective silicon substrate 78, 80. Overlaying substrate 78 is a dielectric layer 82, and similarly, overlaying substrate 80 is a dielectric layer 84. An electrode 86 is disposed adjacent and spaced-apart from the substrate/dielectric layer structures. The electrode 86 is commonly connected to voltage sources 88 and 90. Voltage source 88 is also connected to substrate 78, and voltage source 90 is connected to substrate 80.

The application of voltages V1 and V2 between the substrates 78, 80 and electrode 86 results in a reversible electrical force in the immediate vicinity of the surface of the dielectric layers 82, 84 acting to hold the ends of the cell. Through orientation-dependent etch techniques, the substrate 80 underlying depression 76 can be uniformly thin to form a deformable membrane. Thus, upon contraction of the muscle cell, the membrane-thin substrate 80 deforms as it is drawn towards the muscle cell. This deformation can be measured by a variety of optical and electrical means. One such means is that shown in FIG. 3, which involves measuring directly the change in capacitance resulting from the increased mean spacing between metal films 92 and 94 which are separated by a dielectric film 96.

Dielectric film 96 is suitably a layer of glass. The glass layer serves to hold the top portion of the capacitance device in juxtaposition with the lower portion 100. The glass layer can be formed using conventional sintered infused glass techniques employed in hybrid circuit processing. The capacitive device and measurement system may suitably be in accordance with that disclosed in Sander et al., "MONOLITHIC CAPACITANCE PRESSURE TRANSDUCER-IC WITH PULSE PERIOD OUTPUT", IEEE/Engineering in Medicine and Biology Conference on Frontiers of Engineering and Health Care, 1979, pages 189–192.

Isometric force production which occurs with no change in muscle length may also be measured using device 70 by connecting a voltage source 102 between the metal film plates 92, 94 of the capacitor so as to create an electrical force which tends to pull the plates together. The voltage required to maintain the distance between the metal film plates is a function of the force producted by the muscle cell acting to deform the substrate membrane. Accordingly, measurement of the isometric force production parameters of the muscle cell can be made.

Other means for direct readout of muscle length might be an optical means in which light, for example a laser beam, is defracted by the muscle cell. In addition, the extent of the defraction changes which occur during a cell contraction could be used to control the voltage source 102 so as to maintain a constant muscle length.

Figure 4:
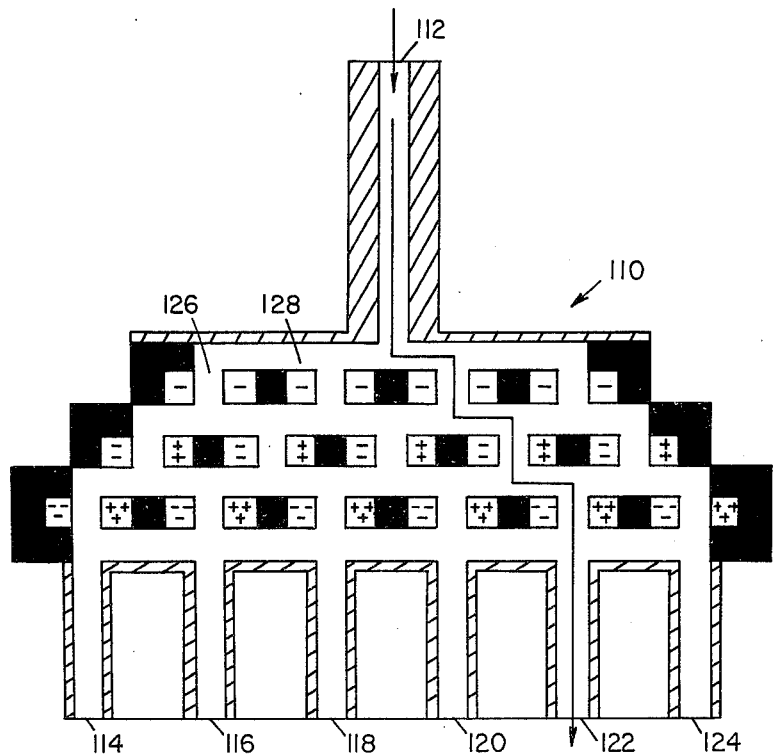
FIG. 4 is a schematic diagram of a device in accordance with the present invention for chromatographic separation of cells or micromolecules.

Referring now to FIG. 4, there is shown an embodiment of the surface field effect device of the present invention for chromatographic separation of cells or macromolecules. The device 110 shown in FIG. 4 has an inlet port 112 and a plurality of outlet ports 114, 116, 118, 120, 122 and 124. The view shown in FIG. 4 is a plan view of the device illustrating the device body and the channel grooves therethrough. Device 110 is fabricated using standard orientation-dependent etch techniques, which provides for the formation of grooves defining channel paths 126 in and around lands 128. Furthermore, fabrication of device 110 involves formation of the lands 128 with electrically-isolated semiconductor regions. Currently-used dielectric isolation techniques may be utilized to produce the electrically-isolated semiconductor regions. Device 110 would further include a dielectric cover, for example, a nitrided silicon slice, attached by sintered glass bonding to create a fluid tight container within device 110. Electric contact and metallization to the individual regions of device 110 is accomplished by using standard integrated circuit fabrication techniques.

As indicated in FIG. 4, the semiconductor regions of the lands are to have voltages of different magnitudes and algebraic signs, such that an electric field is generated across the entire device. This provides the means for applying electrostatic forces at the walls of the channel grooves. The channel groove widths can be sized as desired and made arbitrarily small down to about one micron in dimension. Also, many rows of lands can be formed to increase the flow-path length through the device.

Accordingly, the surface field effect device embodiment shown in FIG. 4 comprises a long path or column length chromatographic device which not only sizes cells or particles according to their physical size but also, because of the capability of applying electrostatic forces along the channel grooves, according to their electrostatic surface charge. Electrostatic surface charge separation is effected because a charged particle attracted to a channel groove wall moves more slowly than one repelled away from the surface. For example, if the channel groove walls have an applied electrical potential so as to strongly attract the cells or particles with negative surface charges greater in magnitude than a chosen value, then the cells or particles will move more slowly than all others of the same size but lesser charge. Therefore, the two populations of cells are separated.

Figure 5:
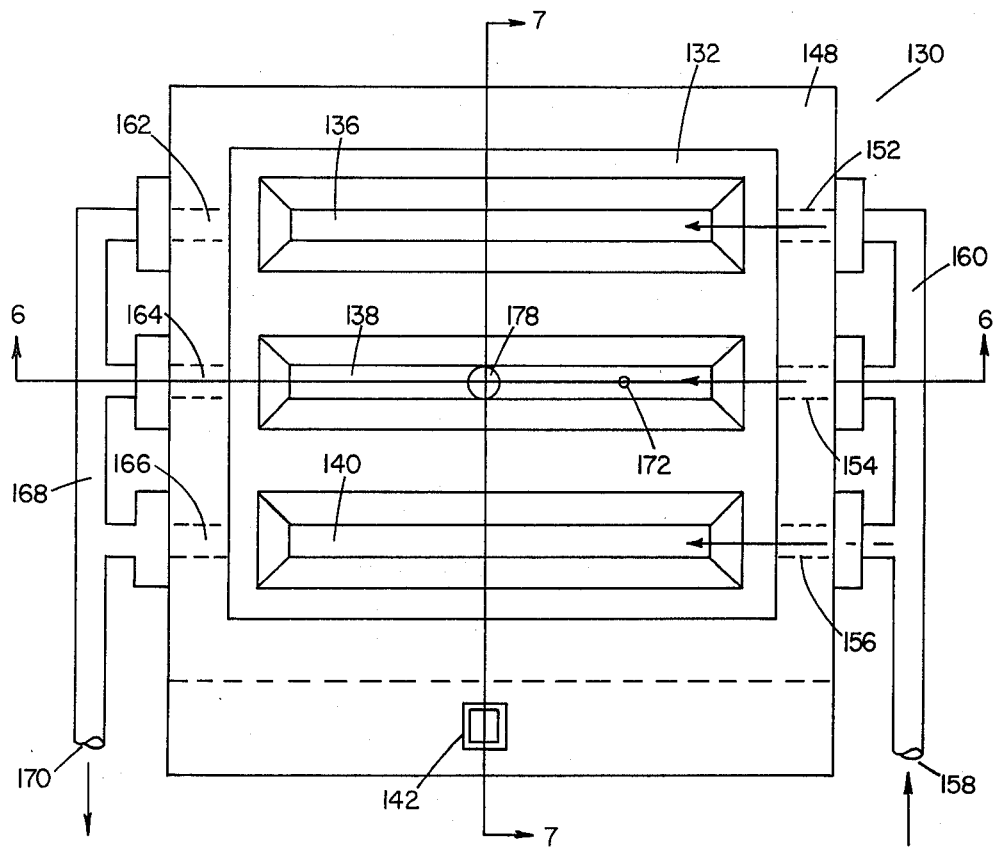
FIGS. 5–7 are schematic diagrams, in plan and section views, of a device in accordance with the present invention for immobilizing a plurality of cells in cell culturing.
Figure 6:
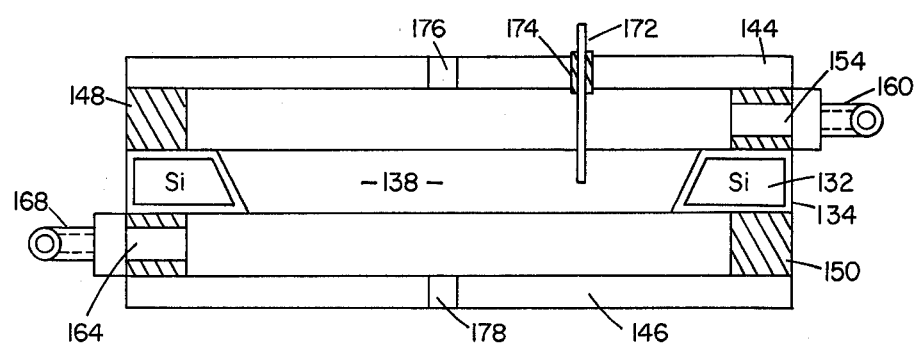
Figure 7:
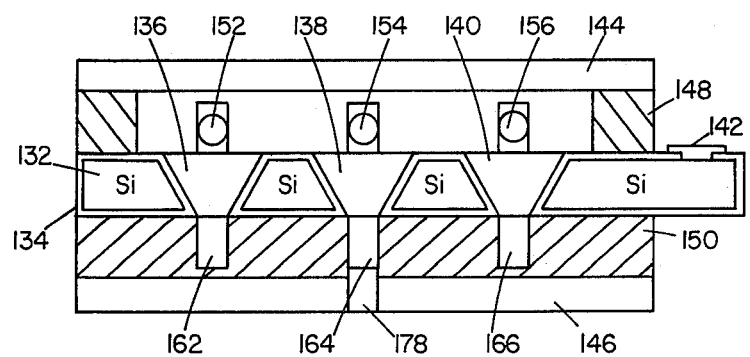

Referring now to FIGS. 5, 6 and 7 there is shown in plan and section views an embodiment of the surface field effect device of the present invention suitable for multiple cell immobilization and the handling of large numbers of cells such as is required in cell culturing. In considering a device for such utility, it is desired that as many cells as possible be accommodated in a minimum of space. Moreover, the cells must be handled in a way which does not alter the characteristics and function of the cells. The utilization of silicon orientation-dependent etching techniques, which provide small and well-defined geometric shapes, makes available in a relatively small device a very large surface area for interaction with cells.

In FIG. 5 surface field effect device 130 is shown in plan view with the top cover plate removed. FIG. 6 shows a section view of device 130 taken along the section lines 6—6 in FIG. 5. Similarly, FIG. 7 shows a section view of device 130 taken along the section line 7—7 in FIG. 5.

Surface field effect device embodiment 130 includes an electrically-conducting substrate 132 such as silicon having an overlying dielectric layer 134. Substrate 132 serves as an electrode in device 130. Substrate 132 is formed with parallel lands and grooves formed using standard slice orientation etch technology. In device embodiment 130, the silicon surrounding all of the groove openings 136, 138 and 140 is at a common electrical potential with electrical contact being achieved by metalization contact 142.

An aqueous cell culture medium is confined within device 130 by upper and lower cover plates 144, 146. The cover places are fixed in place by spacers 148, 150, which may suitably be a dielectric, polymer, or ceramic material.

Access to the interior of device 130 for the introduction of a cell culture medium is by inlet ports 152, 154 and 156 extending through spacer 148. A single inlet to 158 and a manifold 160 may suitably be utilized to distribute and supply the cell culture medium to each inlet port. Removal of the cell culture medium from device 130 is through outlet ports 162, 164 and 166. In communication with the outlet ports is an outlet manifold 168 having a single outlet tube 170.

A control electrode 172 is inserted through top cover plate 144. The surface of electrode 172 is in physical contact with the cell culture medium inside device 130. A seal 174 is further provided around electrode 172. Electrode 172 may suitably comprise a metal rod, such as platinized platinum.

As an additional feature, the device 130 may include optically-transparent windows 176, 178 to provide for the taking of optical measurements to monitor the characteristics of the cells inside the device. The optically transparent windows can comprise the entire upper and lower boundary plates and be composed of a suitably optically transparent material, such as glass.

It will, of course, be understood that a source of electrical power is connected across device 130 between electrodes 142 and 172. Upon the connection of electrical power to the device, an electric field is generated between the electrodes which extends into the culture medium in the grooves 136, 138 and 140 and provides the mechanism for cell control.

It is to be understood that the above-described device embodiments are only illustrative of the principles of the present invention, and that numerous other embodiments may be devised by those skilled in the art for particular applications.

What is claimed is:

1. A device for physically interacting with charged species particles, which comprises:
    a chamber;
    a semiconductor substrate electrode;
    a silicon-based dielectric layer overlaying said semiconductor substrate electrode to define a first boundary;
    a metal electrode disposed opposite said dielectric layer to define a second boundary;
    an electrically-conductive fluid in the chamber containing charged species particles, said fluid interfacing with the dielectric layer at the first boundary surface and interfacing with the metal electrode at the second boundary; and
    a controllable source of electrical potential connected to said electrodes establishing an electric field within the fluid to impose an electrostatic force on the charged species particles therein for selectively attracting, holding and repelling particles relative to the first interface boundary.

2. The device of claim 1 wherein the semiconductor substrate comprises silicon.

3. The device of claim 1 wherein the controllable electrical potential source comprises a variable output voltage DC power supply.

4. A device for physically interacting with charged species particles to separate the same according to surface charge and size, comprising:
    a chamber;
    at least first and second adjacent semiconductor substrate electrodes;
    a separate silicon-based dielectric layer overlaying each of said semiconductor substrate electrodes and defining interface boundaries;
    means for isolating said semiconductor substrate electrodes and overlaying dielectric layers one from another;
    a single metal electrode disposed opposite said dielectric layers, said metal electrode defining an interface boundary;
    an electrically-conductive fluid in the chamber containing charged species particles, said fluid contacting the dielectric layers at the interface boundaries defined thereby, and contacting the metal electrode at the interface boundary defined thereby;
    means connected between said semiconductor substrate electrodes and said metal electrode, for applying different electrical potentials between each of said semiconductor substrate electrodes and said metal electrode, so as to establish different electric fields in separate regions of said fluid and impose an electrostatic force on the charged species particles in the fluid, whereby certain of the particles are attracted and repelled relative to one of the dielectric layers dependent upon the charge of the particles; and
    means for producing a laminar flow of the fluid within said chamber so as to impose a translational force on the particles in the fluid, whereby a separation of the particles according to size is effected.

5. A device for physically interacting with a single cell carrying a net electric charge to hold the same, which comprises:
    a semiconductor substrate electrode configured by etching to have a depression therein;
    a silicon-based dielectric layer overlaying said substrate electrode and conforming to the depression etched therein so as to define a receptacle for a portion of a cell to be held;
    a metal electrode disposed adjacent and spaced-apart from said dielectric layer;
    an electrically-conductive fluid containing a cell to be held, said fluid being in contact with said dielectric layer and with said metal electrode; and
    means for establishing an electric field within said fluid to impose a force on the charged cell which attracts and holds the cell in the receptacle.

6. A device for chromatographic separation of charged species particles, comprising:
    a device body having a plurality of grooves formed therein to define interconnecting channel paths therethrough and define lands between the channel grooves;
    first and second electrically-isolated semiconductor regions formed on each of said lands;
    a cover of a silicon-based dielectric material overlaying said device body to make said grooves into fluid tight container regions;
    means for defining a fluid inlet port to said device body in fluid communication with said interconnecting channel paths;
    means for defining a plurality of fluid outlet ports from said device body in fluid communication with said interconnecting channel paths;
    an electrically-conductive fluid containing charged species particles introduced into the device body channel paths through the fluid inlet port;
    means connecting to each of said semiconductor regions for establishing an electrical potential thereon, so as to produce electric fields in said fluid that impose electrostatic forces on charged species particles in the fluid as it passes through said device body, whereby certain of the charged species particles move more slowly through the device body and exit an outlet port at a different time from other charged species particles in the fluid.

7. A device for physically interacting with a plurality of charged species particles to immobilize the same, comprising:
    a semiconductor substrate formed with a plurality of lands and groove openings;
    a silicon-based dielectric layer overlaying said substrate and defining a boundary layer;
    an electrically-conductive fluid containing charged species particles and interfacing with the dielectric layer boundary interface;
    an outlet port for discharging fluid out of the chamber;
    a metal electrode disposed within the chamber so as to be in physical contact with fluid therein;

means for establishing an electrical contact to said metal electrode; and a controllable source of electrical potential connected to said metal electrode contact means and said substrate contact means, for establishing an electric field within said fluid to impose an electrostatic force on the charged particles therein for selectively attracting, holding and repelling particles relative to the dielectric layer boundary interface.

* * * * *